United States Patent [19]

Schlier et al.

[11] Patent Number: 5,400,791
[45] Date of Patent: Mar. 28, 1995

[54] INFRARED FUNDUS VIDEO ANGIOGRAPHY SYSTEM

[75] Inventors: Robert Schlier, Concord, Mass.; Mark Furlong, Kingston, N.H.; Michael Lesiecki, Natick, Mass.; Joseph Canter, Lexington, Mass.; Ulrich Klingbeil, Belmont, Mass.

[73] Assignee: Candela Laser Corporation, Wayland, Mass.

[21] Appl. No.: 775,173

[22] Filed: Oct. 11, 1991

[51] Int. Cl.$^6$ .......................... A61B 6/00; A61B 5/00
[52] U.S. Cl. .................................... 128/664; 128/633
[58] Field of Search .............. 128/633, 664, 665, 395; 351/206, 211, 221

[56] References Cited

U.S. PATENT DOCUMENTS

| | | |
|---|---|---|
| 3,828,788 | 8/1974 | Krasnov et al. . |
| 3,883,752 | 5/1975 | Davies et al. ............ 307/88.3 |
| 4,402,601 | 9/1983 | Riva . |
| 4,423,931 | 1/1984 | Shapiro . |
| 4,579,430 | 4/1986 | Bille .................. 128/691 X |
| 4,638,800 | 1/1987 | Michel ................ 128/303.1 |
| 4,759,360 | 7/1988 | Nakanishi et al. ......... 128/395 X |
| 4,776,335 | 10/1988 | Nakanishi et al. ......... 128/395 X |
| 4,854,691 | 8/1989 | Sekine et al. . |
| 5,047,638 | 9/1991 | Cameron et al. .............. 250/330 |
| 5,048,946 | 9/1991 | Sklar et al. ............... 128/633 X |
| 5,152,295 | 10/1992 | Kobayashi et al. .............. 128/665 |

FOREIGN PATENT DOCUMENTS

| | | |
|---|---|---|
| 0161703 | 11/1985 | European Pat. Off. . |
| 0380221 | 8/1990 | European Pat. Off. . |
| 4126329A1 | 3/1992 | Germany . |
| 4141087A1 | 6/1992 | Germany . |
| 62-271481 | 11/1987 | Japan . |
| 8301049 | 7/1984 | Netherlands . |

OTHER PUBLICATIONS

Turk et al., British Journal of Photography Sep. 1978 "Clinical Indocyanine Green Fluorescence . . .".
Benson et al., Phys. Med. Biol. 1978, vol. 23 (1) pp. 159–163, "Fluorescence Properties of Indocyanine . . .". International Search Report.
Flower, R. W. et al., Consideration of Equipment Used For Recording and Analyzing ICG Choroidal Angiograms.
Zeimer, R. C. et al., Visualization of the Retinal Microvasculature by Targeted Dye Delivery.
Wiggins R. L. et al., Holography Using a Fundus Camera.
Riva, C. E. et al., Fundus Camera Based Retinal LDV.
Scheider and Schroedel, High Resolution Indocyanine Green Angiography With a Scanning Laser Opthalmoscope.

*Primary Examiner*—David Isabella
*Assistant Examiner*—Elizabeth M. Burke
*Attorney, Agent, or Firm*—Testa, Hurwitz & Thibeault

[57] ABSTRACT

An infrared fundus angiography camera and ICG angiography imaging procedure for improved visualization and diagnosis of vascular diseases of the eye, especially SRNV, features a narrow bandwidth non-coherent and decollimated infrared illumination source, an optical system for directing the infrared illumination onto the retina and for directing the resulting retinal image toward an image storage device, and an optical filter positioned between the retina and the image storage device for blocking the infrared illumination from entering the image storage device. An infrared laser produces infrared illumination and a opal glass, fiber array, or integrating sphere light diffuser positioned between the infrared laser and the optical system decollimates and makes the infrared illumination incoherent. The laser includes a temperature stabilized infrared laser diode having an output matched to the excitation peak of an infrared fluorescent dye, such as ICG. The fundus camera includes an optical filter in the emission image path having a sharp cut-off response matched to the excitation and emission peaks of the infrared dye so that the filter substantially passes emission peak wavelengths and substantially blocks excitation peak wavelengths.

50 Claims, 3 Drawing Sheets

INFRARED FUNDUS VIDEO ANGIOGRAPHY SYSTEM

BACKGROUND OF THE INVENTION

Age related macular degeneration (AMD) is the most frequent disease causing loss of vision in adults aged 50 and over. The formation of new blood vessels, subretinal neovascularization (SRNV), creates the visual impairment. Treatment is not possible in a large percentage of cases because SRNV often underlays the fovea and treatment would severely damage central vision, and, because the SRNV is often difficult to visualize and diagnose with conventional ophthalmic instrumentation.

One method of visualizing the fundus involves injecting the patient with a fluorescent dye agent which enters the blood vessels of the eye fundus and generates a fluorescence emission image of the vessels when excited by a particular wavelength of light. One such dye is Sodium Fluorescein which requires blue light to excite a fluorescent emission. However, since blue light does not deeply penetrate the retina, Sodium Fluorescein is only able to image vessels on or near the surface of the retina.

Indocyanine green (ICG) is a well known water soluble tricarbocyanine dye that binds almost 100% to protein in the blood and fluoresces in the near infrared which is capable of deeply penetrating the retina. Infrared ICG angiography highlights the choroidal vasculature with limited obstruction from retinal processes, including hemorrhages or leakages, or the retinal pigmented epithelium (RPE) layer overlaying the choroid. Furthermore, infrared ICG angiography allow immediate monitoring of areas of the retina that have been recently treated to confirm vessel closure.

However, due to its relatively low fluorescence intensity of only about 4%, relatively high intensity illumination from a conventional angiography light source is necessary to excite ICG to produce useful fluorescence emission images. This requires exposing the retina to high intensity broadband irradiation, of up to 200 mw/cm$^2$, capable of damaging the retina.

SUMMARY OF THE INVENTION

The present invention provides an infrared fundus camera and angiography imaging procedure for improved visualization and diagnosis of vascular diseases of the eye, especially SRNV. This invention allows for infrared ICG angiography to highlight the choroidal vasculature of the eye with limited obstruction from retinal processes including hemorrhages or leakage. The device also has features of a general purpose funduscope for dynamic and static imaging which allows general assessment of the patient's retina.

In general, in one aspect, this invention features a fundus camera and method for imaging the retina including a narrow bandwidth non-coherent and decollimated infrared illumination source, an optical system for directing the infrared illumination onto the retina and for directing the resulting retinal image toward an image storage device, and an optical filter positioned between the retina and the image storage device for blocking the infrared illumination from entering the image storage device.

Preferred embodiments include an infrared laser for producing infrared illumination and a light diffuser positioned between the infrared laser and the optical system for decollimating and making the infrared illumination incoherent. The laser includes a temperature stabilized infrared-laser diode having an output matched to the excitation peak of an infrared fluorescent dye, such as ICG.

In other preferred embodiments, the fundus camera includes an optical filter in the image path having a sharp cut-off response matched to the excitation and emission peaks of the infrared dye so that the filter substantially passes emission peak wavelengths and substantially blocks excitation peak wavelengths. In one preferred embodiment the infrared dye is ICG and the filter effectively blocks wavelengths below about 820 nm.

In yet other preferred embodiments, the light diffuser includes opal glass, a fiber array, or an integrating sphere. The image storage device includes a high resolution, high sensitivity video camera which operates in conjunction with a continuous illumination source to provide real time video recording.

Thus, the invention described herein offers the advantages of allowing assessment of deeper retinal and subretinal tissue layers through the use of infrared light which penetrates deeper into the retina than light which is normally used for other angiographic dyes, such as sodium fluorescein. The infrared laser and diffuser offer the advantages of providing a highly efficient excitation source for the ICG dye, thus allowing minimal irradiation of the retina and efficient isolation of the illumination from the emission image with an optical filter.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being place upon illustrating the principles of the invention.

DESCRIPTION OF PREFERRED EMBODIMENT

Figure 1:
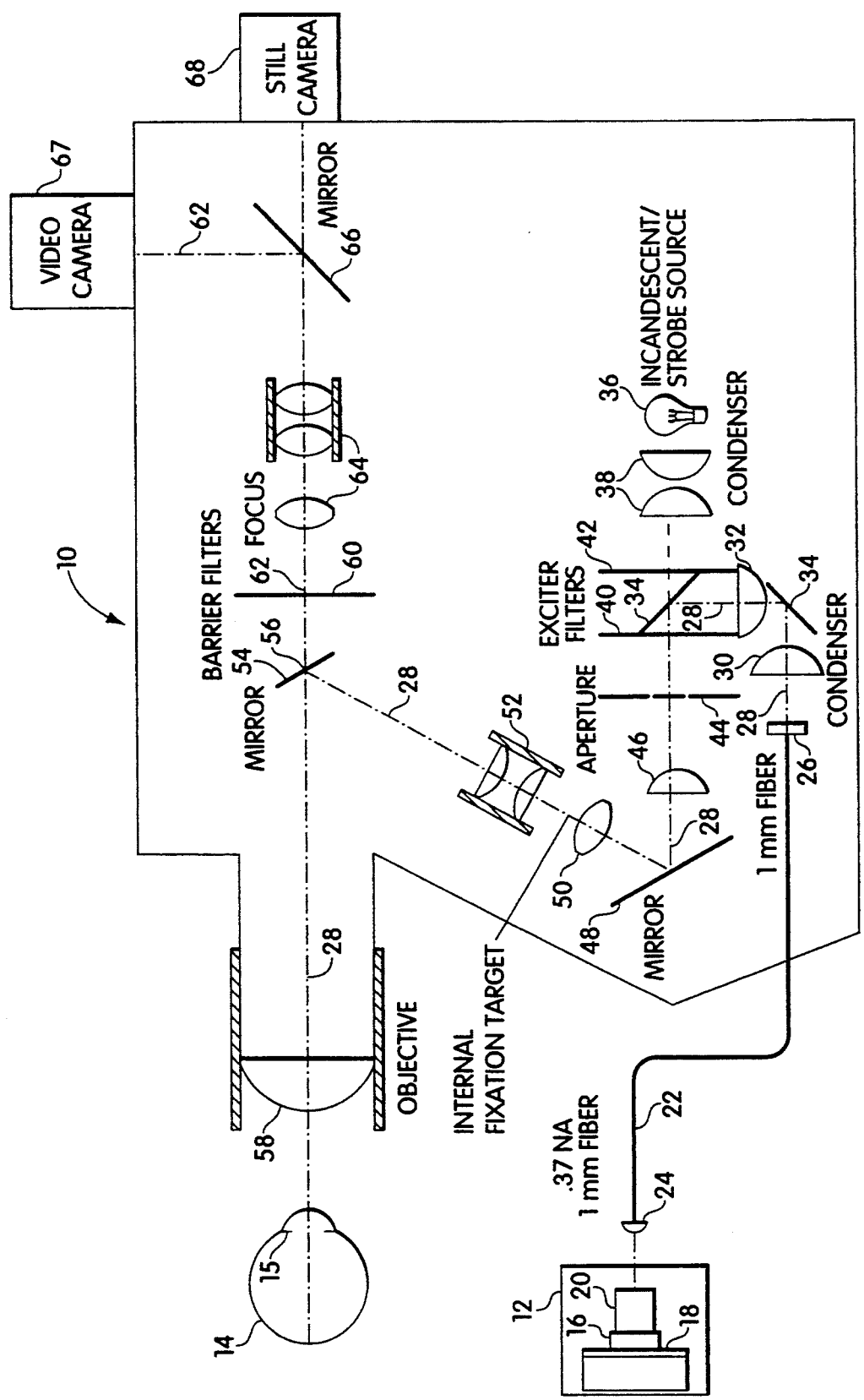
FIG. 1 shows a schematic diagram of the infrared fundus video angiography camera of this invention.

FIG. 1 shows a schematic diagram of the infrared fundus video angiography camera 10 of this invention which is capable of high speed infrared ICG angiography. Fundus camera 10 includes an infrared laser light source 12 to illuminate the retina of the eye under examination 14 and thereby excite ICG dye present in the fundus of the eye to produce high quality fluorescence emission images of the fundus. The narrow band wavelength output of infrared laser light source 12 is tuned to provide efficient excitation of the ICG dye and thereby minimize the irradiation of the retina required to cause fluorescence of the dye.

Figure 2:
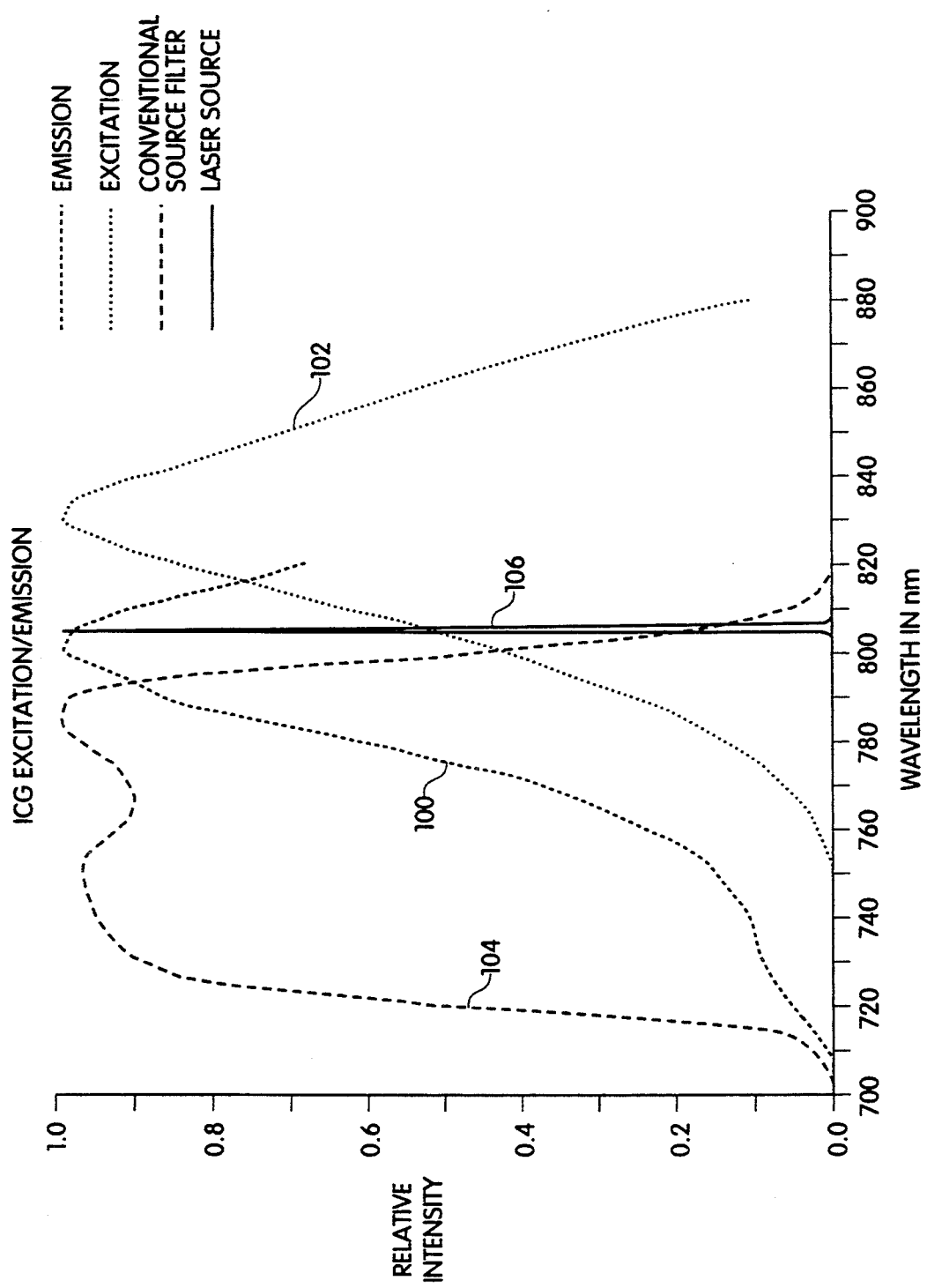
FIG. 2 shows a graph of the ICG dye excitation and emission curves relative to the infrared laser illumination source of the angiography camera of FIG. 1.

FIG. 2 shows the infrared ICG excitation and emission characteristics graphed as relative illumination intensity versus the wavelength of light in nanometers (nm). The ICG excitation curve 100 indicates the relative sensitivity of ICG to an illumination source to cause a fluorescent emission response from the dye. Excitation curve 100 shows that ICG has peak sensitivity to excitation illumination having a wavelength of between approximately 785 nm and 815 nm. Furthermore, ICG experiences a sharp roll-off of sensitivity to excitation illumination outside that band of wavelengths.

The ICG emission response curve 102 shows that ICG produces fluorescent emissions over a narrow band of wavelengths centered at approximately 830 nm. The emission response curve shows maximal fluorescent emission in the band of wavelengths between approximately 820 nm and 840 nm, and falls off rapidly outside that range.

FIG. 2 also shows a spectral curve 104 for a conventional broadband incandescent angiography light source, typically having a bandwidth of 50 nm to 100 nm. The spectral curve shows that the output intensity of this broadband source falls off rapidly at wavelengths above about 790 nm, which also corresponds to the wavelength of peak excitation sensitivity of the ICG dye. Also, most of the light from the conventional source is of wavelengths below that of the excitation band. Thus, this broadband source requires a high overall, and possibly harmful, intensity to be effective at the ICG excitation wavelengths, whereas an excitation source at a wavelength centered within the excitation sensitivity curve of ICG is more efficient and requires a relatively low overall intensity.

The narrow band output of infrared laser light source 12 (FIG. 1) is shown by spectral curve 106 to be located near the peak of the ICG sensitivity characteristic curve, i.e., at about 805 nm, and has a bandwidth (80%) of about 1 nm. Other infrared sources may be used as long as the bandwidth can be controlled to less than about 10 nm. Since the laser light source has a high peak intensity concentrated near the peak of the ICG excitation sensitivity curve, the laser acts as an efficient illumination source for exciting the ICG dye. The overall illumination intensity required from the laser source to produce a usable ICG emission response is much less, by a factor of at least about 10, than the excitation intensity required from the conventional broadband source having the spectral output of shown by curve 104. Thus, the laser source provides highly efficient, low overall intensity, excitation of ICG dye within the eye, without harm to the eye.

Furthermore, since the laser illumination source produces a very narrow bandwidth of output wavelengths, a steep-edged optical filter having a sharp roll-off below approximately 820 nm may be used to effectively isolate the laser excitation illumination (805 nm) from the fluorescent emission response (830 nm) and further enhance emission image contrast and quality. Thus, the use of a sharp-edged filter close to the source wavelength in this case filters out essentially the entire source illumination.

Although the infrared laser light source 12 appears to be ideal for ICG infrared angiography, the coherency and collimation of the laser light source create obstacles which must be overcome before successful ICG angiography is achieved. The coherency of the laser light source causes "speckling" which degrades the angiography image. The collimated nature of the laser light source produces a "hot spot" which is inappropriate for illuminating the relatively large area encompassed by the fundus. These obstacles are overcome by the present invention through the use of a light diffuser in the laser source output path to produce an extended (i.e., decollimated), incoherent, narrow band light source from the collimated, coherent, narrow band infrared light emitted by the laser.

Referring again to FIG. 1, the infrared laser excitation source 12 includes an infrared laser diode 16 mounted on a heat sink 18 to temperature stabilize the wavelength of the laser diode output. Laser diode 16 nominally produces 250 mw output at 805 nm and has an 80% bandwidth of about 1 nm. A 250 mw laser source is required to deliver approximately 10 mw of illumination power into the eye when taking into account various system losses.

The heat sink 18 increases the temperature stability of the laser diode to provide less than 10 nm maximum wavelength shift over a 30° C. temperature range, i.e., 795 nm to 815 nm. This temperature stability assures that the infrared laser output will remain within the band of optimal excitation sensitivity for the ICG dye, as shown by ICG sensitivity curve 100 of FIG. 2, while also remaining below the 820 nm cut-off of the sharp-edged filter to be used to isolate the excitation illumination from the fluorescent emission.

The infrared laser light output from laser diode 16 passes through a collimator 20 and is optically coupled through a coupling lens 24 to a 1 mm diameter optical fiber link 22. The end of the fiber may be illuminated at an angle to create an annular illumination pattern at the fiber output. The infrared laser light is transferred by the optical fiber link 22 into the fundus camera 10 and is coupled to the optical system of the fundus camera through a light diffuser 26. Light diffuser 26 acts to decollimate the laser light and eliminate its coherency. In one preferred embodiment the light diffuser is opal glass. In another preferred embodiment the light diffuser is a fiber array, and in yet another preferred embodiment the light diffuser is an integrating sphere.

The infrared light output from diffuser 26 passes along illumination path 28 through condenser lenses 30, 32, and mirror 34 for collecting the diverging light output from the light diffuser.

The infrared light output from lens 32 strikes a dichroic mirror 34 and is redirected along the continuation of the illumination path 28. Dichroic mirror 34 is matched to the wavelength of the infrared laser light source 12 to reflect the laser light source, yet pass other wavelengths of light, e.g., the broadband light output from a conventional incandescent source.

A conventional incandescent/strobe source of broadband light 36, which acts as an alternate source of illumination, is located along the illumination path behind the dichroic mirror 34 so that its illumination passes through a set of condenser lenses 38, through the dichroic mirror 34, and along illumination path 28. A set of exciter filters 40 and 42 may be placed into the illumination path for use with the conventional light source 36, but are removed from the illumination path when the infrared laser is used as the illumination source.

The infrared laser illumination reflected by dichroic mirror 34 (or the conventional incandescent illumination passing through the dichroic mirror) next passes through an aperture 44 which has a central portion blocked to produce a "donut" or annular ring, illumination pattern. The optical system of the fundus camera provides that the focal plane of aperture 44 is conjugate to the focal plane of the pupil 15 of the eye under examination 14 so that it produces a 5 to 6 mm diameter ring of illumination at the focal plane of the pupil.

The infrared illumination passing out of aperture 44 is directed along the illumination path 28 by relay optics 46, 50, 52, and mirror 48, which image the aperture 44 onto a mirror 54 having a 5 to 6 mm diameter central opening 56. The optical system of the fundus camera provides that the focal plane of mirror 56 is also conjugate to the focal planes of both the aperture 44 and the pupil 15, i.e., the central opening in the mirror is coincident with the center of the illumination ring. Thus, infrared illumination which would otherwise pass through central opening 56 has been effectively blocked by aperture 44.

Mirror 54 redirects the ring of infrared illumination toward the eye along illumination path 28 and through an aspheric ophthalmic objective lens 58 which images the mirror onto the pupil such that the image on the mirror is conjugate to the image formed at the pupil by the objective lens. Thus, the ring of illumination formed by the aperture and reflected by mirror 56 forms a corresponding illumination ring at the focal plane of the pupil having a hole corresponding to the central opening of the pupil through which the emission image from the retina will pass.

The illumination ring formed at the focal plane of the pupil passes through the pupil to uniformly illuminate the retina with diffused infrared light, i.e., the light diffuser is imaged onto the retina, which excites the ICG dye to produce a fluorescent emission from the blood vessels to be imaged.

The fluorescent emission image generated by the blood vessels of the retina pass through the pupil and back along illumination path 28 through objective lens 58 toward mirror 54. The emission image passes through the central opening 56 in mirror 54 to impinge on a barrier filter 60.

Barrier filter 60 is an optical filter matched to the IGC excitation and emission characteristics, having a sharp roll-off below 820 nanometers which effectively isolates any stray or reflected infrared illumination (805 nm) from the fluorescent emission image (830 nm) returning from the retina. A typical matched filter response for use in this case would have 100% optical blockage (i.e., $<10^{-4}$ transmission) at wavelengths less than about 820 nm, and will be transmissive (i.e., >80% transmission) at wavelengths greater than about 820 nm. This filter effectively increases the sensitivity of the imaging system to produce high contrast images since the relatively strong illumination source has been isolated from the relatively weak emission image.

The emission image passes through barrier filter 60, travels along image path 62, through imaging optics 64, and impinges on a directing mirror 66. Directing mirror 66 may be left in the imaging path to redirect the image toward a high resolution, high sensitivity video camera 67, or other imaging system, capable of capturing infrared images. Alternatively, mirror 66 may be removed from the imaging path 66 so that an infrared still camera 68 may be used to capture the returning emission images.

Figure 3:
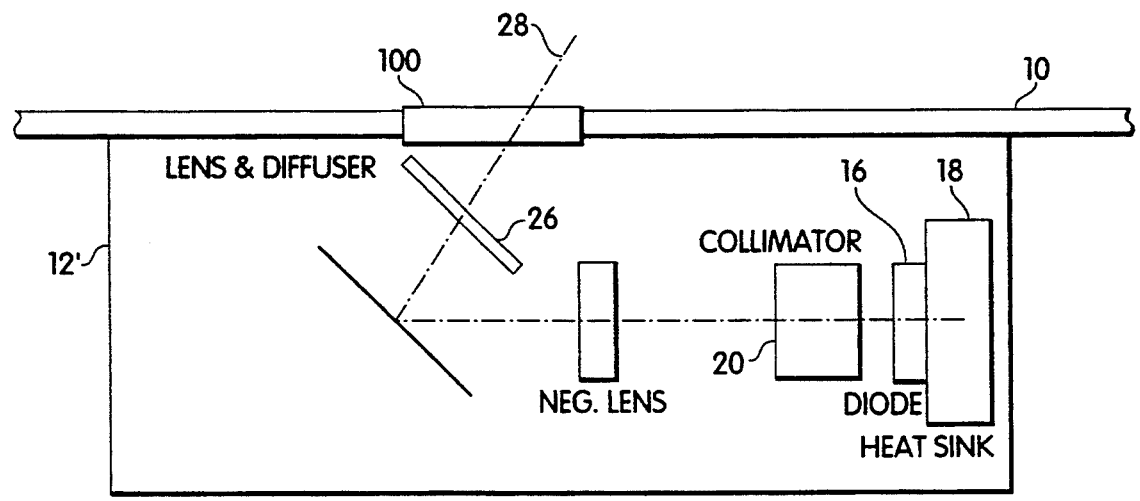
FIG. 3 shows an alternative preferred embodiment of the infrared laser source directly coupled to the body of the angiography camera of FIG. 1 and using an opal glass or fiber array light diffuser.

FIG. 3 shows an alternative preferred embodiment of an infrared laser 12' which is directly coupled to the fundus camera 10 through a port 100 in the side of the fundus camera, rather than through a fiber optic link. Here, the opal glass or fiber array light diffuser 26 is located in the illumination path 28 between the laser diode 20 and the optics of the fundus camera.

Figure 4:
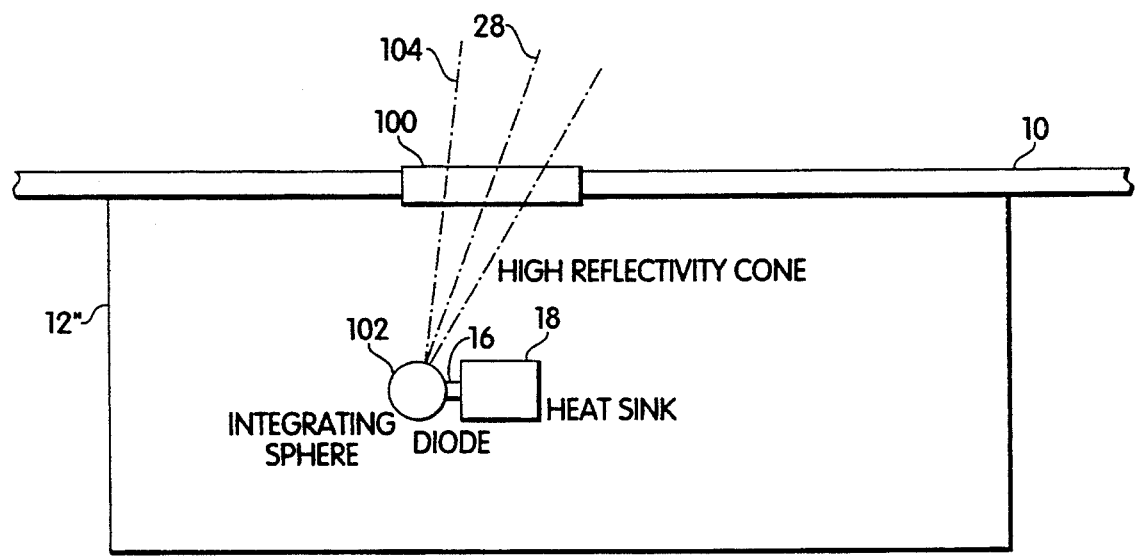
FIG. 4 shows an alternative preferred embodiment of the infrared laser source directly coupled to the body of the angiography camera of FIG. 1 and using an integrating sphere light diffuser.

FIG. 4 shows yet another alternative preferred embodiment of an infrared laser 12" also directly coupled to fundus camera 10. Here, an integrating sphere 102 is coupled between the laser diode 20 and the illumination path 28 to decollimate and reduce the coherency of the laser illumination. Laser light which enters the sphere bounces around in a confused manner inside the highly reflective sphere before emerging in a diverging cone of light 104 along the illumination path. The integrating sphere produces light which is more homogenous than that produced by the opal glass or fiber array diffuser, but is also less intense.

While this invention has been particularly shown and described with reference to preferred embodiments thereof, it will be understood by those skilled in the art that various changes in form and details may be made therein without departing from the spirit and scope of the invention as defined by the appended claims. For instance, other types of infrared fluorescent agents exhibiting similar characteristics may be substituted for ICG. Virtually any video imaging system may be used to capture the emission images, including digital image storage and retrieval, real-time VCRs, etc.

We claim:

1. An apparatus for imaging a retina, comprising:
   a narrow bandwidth, non-coherent, and decollimated infrared illumination-producing illumination source;
   an optical system for directing narrow bandwidth, non-coherent, and decollimated infrared illumination produced by the source onto the retina of an eye under examination and for directing a resulting retinal image toward an image storage device; and
   an optical filter positioned between the retina and the image storage device for blocking the infrared illumination from entering the image storage device;
   wherein the illumination source comprises
      an infrared laser for producing infrared illumination and
      a light diffuser positioned between the infrared laser and the optical system for decollimating and making the infrared illumination incoherent.

2. The apparatus of claim 1, wherein the infrared laser comprises an infrared laser diode.

3. The apparatus of claim 2, wherein the infrared laser diode is temperature stabilized.

4. The apparatus of claim 1 wherein the diffuser includes opal glass.

5. The apparatus of claim 1 wherein the diffuser includes a fiber array.

6. The apparatus of claim 1 wherein the diffuser includes an integrating sphere.

7. The apparatus of claim 1 wherein the narrow bandwidth, non-coherent, and decollimated infrared illumination produced by the illumination source has an 80% bandwidth of less than about 10 nanometers.

8. The apparatus of claim 7 wherein the 80% bandwidth is between about 1 nanometer and about 10 nanometers.

9. The apparatus of claim 8 wherein the 80% bandwidth is about 1 nanometer.

10. An apparatus for imaging a retina, comprising:

a narrow bandwidth, non-coherent, and decollimated infrared illumination-producing illumination source which is matched to an excitation peak of ICG dye;

an optical system for directing narrow bandwidth, non-coherent, and decollimated infrared illumination, which is produced by the source and matched to the excitation peak of the ICG dye, onto the retina of an eye under examination and for directing a resulting retinal image toward an image storage device; and an optical filter positioned between the retina and the image storage device for blocking the infrared illumination from entering the image storage device.

11. The apparatus of claim 10 wherein the illumination source provides narrow band illumination having wavelengths between 795 nm and 815 nm.

12. The apparatus of claim 11 wherein the illumination source provides illumination having an 80% bandwidth of about 10 nm or less.

13. The apparatus of claim 10 wherein the optical filter has a sharp cut-off response matched to excitation and emission peaks of the ICG dye so that the filter substantially passes emission peak wavelengths and substantially blocks excitation peak wavelengths.

14. The apparatus of claim 13 wherein the optical filter blocks wavelengths below 820 nm.

15. The apparatus of claim 10, wherein the illumination source comprises:
an infrared laser for producing infrared illumination; and
a light diffuser positioned between the infrared laser and the optical system for decollimating and making the infrared illumination incoherent.

16. The apparatus of claim 15, wherein the infrared laser comprises an infrared laser diode.

17. The apparatus of claim 16, herein the infrared laser diode is temperature stabilized.

18. The apparatus of claim 10 wherein the image storage device includes a video camera.

19. The apparatus of claim 18 wherein the illumination source operates continuously to provide for real time video recording by the video camera.

20. The apparatus of claim 10 wherein the narrow bandwidth, non-coherent, and decollimated infrared illumination produced by the illumination source has an 80% bandwidth of less than about 10 nanometers.

21. The apparatus of claim 20 wherein the 80% bandwidth is between about 1 nanometer and about 10 nanometers.

22. The apparatus of claim 21 wherein the 80% bandwidth is about 1 nanometer.

23. An apparatus for imaging a retina, comprising:
a narrow bandwidth, non-coherent, and decollimated infrared illumination-producing illumination source which is matched to an excitation peak of an infrared fluorescent dye having separate excitation and emission peak wavelengths;
an optical system for directing narrow bandwidth, non-coherent, and decollimated infrared illumination, which is produced by the source and matched to the excitation peak of the infrared fluorescent dye, onto the retina of an eye under examination and for directing a resulting retinal image toward an image storage device; and
an optical filter positioned between the retina and the image storage device for blocking the infrared illumination from entering the image storage device, the optical filter having a sharp cut-off response matched to the excitation and emission peaks of the infrared fluorescent dye so that the filter substantially passes emission peak wavelengths and substantially blocks excitation peak wavelengths.

24. The apparatus of claim 23, wherein the illumination source comprises:
an infrared laser for producing infrared illumination; and
a light diffuser positioned between the infrared laser and the optical system for decollimating and making the infrared illumination incoherent.

25. The apparatus of claim 24, wherein the infrared laser comprises a temperature stabilized infrared laser diode.

26. The apparatus of claim 23 wherein the infrared fluorescent dye is ICG dye.

27. The apparatus of claim 23 wherein the illumination source provides narrow band illumination having wavelengths between 795 nm and 815 nm.

28. The apparatus of claim 27 wherein the illumination source provides illumination having an 80% bandwidth of about 10 nm or less.

29. The apparatus of claim 23 wherein the image storage device includes a video camera.

30. The apparatus of claim 23 wherein the narrow bandwidth, non-coherent, and decollimated infrared illumination produced by the illumination source has an 805 bandwidth of less than about 10 nanometers.

31. The apparatus of claim 30 wherein the 80% bandwidth is between about 1 nanometer and about 10 nanometers.

32. The apparatus of claim 31 wherein the 80% bandwidth is about 1 nanometer.

33. An apparatus for imaging a retina, comprising:
a narrow bandwidth, non-coherent, and decollimated infrared illumination-producing illumination source;
an optical system for directing narrow bandwidth, non-coherent, and decollimated infrared illumination produced by the source onto the retina of an eye under examination and for directing a resulting retinal image toward an image storage device which includes a video camera; and
an optical filter positioned between the retina and the image storage device for blocking the infrared illumination from entering the image storage device.

34. The apparatus of claim 33 wherein the illumination source operates continuously to provide for real time video recording by the video camera.

35. The apparatus of claim 34 wherein the infrared fluorescent dye is ICG.

36. The apparatus of claim 35 wherein the optical filter blocks wavelengths below 820 nm.

37. The apparatus of claim 35 wherein the illumination source provides narrow band illumination having wavelengths between 795 nm and 815 nm.

38. The apparatus of claim 37 wherein the illumination source provides illumination having an 80% bandwidth of about 10 nm or less.

39. The apparatus of claim 33 wherein the narrow bandwidth, non-coherent, and decollimated infrared illumination produced by the illumination source has an 80% bandwidth of less than about 10 nanometers.

40. The apparatus of claim 39 wherein the 80% bandwidth is between about 1 nanometer and about 10 nanometers.

41. The apparatus of claim 40 wherein the 80% bandwidth is about 1 nanometer.

42. An apparatus for imaging a retina, comprising:
a narrow bandwidth, non-coherent, and decollimated infrared illumination-producing illumination source comprising an infrared laser diode coupled to a light diffuser, the source matched to an excitation peak of an infrared fluorescent dye having separate excitation and emission peak wavelengths;
an optical system for directing narrow bandwidth, non-coherent, and decollimated infrared illumination, which is produced by the source and matched to the excitation peak of the infrared fluorescent dye, onto the retina of an eye under examination and for directing a resulting retinal image toward an image storage device; and
an optical filter positioned between the retina and the image storage device for blocking the infrared illumination from entering the image storage device, the optical filter having a sharp cut-off response matched to the excitation and emission peak wavelengths of the infrared fluorescent dye so that the filter substantially passes emission peak wavelengths and substantially blocks excitation peak wavelengths.

43. The apparatus of claim 42, wherein the infrared laser diode is temperature stabilized.

44. An apparatus for imaging a retina, comprising:
a narrow bandwidth, non-coherent, and decollimated infrared illumination-producing illumination source comprising an infrared laser coupled to a light diffuser which includes opal glass, the source matched to an excitation peak of an infrared fluorescent dye having separate excitation and emission peak wavelengths;
an optical system for directing narrow bandwidth, non-coherent, and decollimated infrared illumination which is produced by the source and matched to the excitation peak of the infrared fluorescent dye, onto the retina of an eye under examination and for directing a resulting retinal image toward an image storage device; and
an optical filter positioned between the retina and the image storage device for blocking the infrared illumination from entering the image storage device, the optical filter having a sharp cut-off response matched to the excitation and emission peak wavelengths of the infrared fluorescent dye so that the filter substantially passes emission peak wavelengths and substantially blocks excitation peak wavelengths.

45. An apparatus for imaging a retina, comprising:
a narrow bandwidth, non-coherent, and decollimated infrared illumination-producing illumination source comprising an infrared laser coupled to a light diffuser which includes a fiber array, the source matched to an excitation peak of an infrared fluorescent dye having separate excitation and emission peak wavelengths;
an optical system for directing narrow bandwidth, non-coherent, and decollimated infrared illumination, which is produced by the source and matched to the excitation peak of the infrared fluorescent dye, onto the retina of an eye under examination and for directing a resulting retinal image toward an image storage device; and
an optical filter positioned between the retina and the image storage device for blocking the infrared illumination from entering the image storage device, the optical filter having a sharp cut-off response matched to the excitation and emission peak wavelengths of the infrared fluorescent dye so that the filter substantially passes emission peak wavelengths and substantially blocks excitation peak wavelengths.

46. An apparatus for imaging a retina, comprising:
a narrow bandwidth, non-coherent, and decollimated infrared illumination-producing illumination source comprising an infrared laser coupled to a light diffuser which includes an integrating sphere, the source matched to an excitation peak of an infrared fluorescent dye having separate excitation and emission peak wavelengths;
an optical system for directing narrow bandwidth, non-coherent, and decollimated infrared illumination, which is produced by the source and matched to the excitation peak of the infrared fluorescent, onto the retina of an eye under examination and for directing a resulting retinal image toward an image storage device; and
an optical filter positioned between the retina and the image storage device for blocking the infrared illumination from entering the image storage device, the optical filter having a sharp cut-off response matched to the excitation and emission peak wavelengths of the infrared fluorescent dye so that the filter substantially passes emission peak wavelengths and substantially blocks excitation peak wavelengths.

47. An apparatus for imaging a retina, comprising:
a narrow bandwidth, non-coherent, and decollimated infrared illumination-producing illumination source comprising an infrared laser coupled to a light diffuser, the source matched to an excitation peak of an infrared fluorescent dye having separate excitation and emission peak wavelengths;
an optical system for directing narrow bandwidth, non-incoherent, and decollimated infrared illumination, which is produced by the source and matched to the excitation peak of the infrared fluorescent dye, onto the retina of an eye under examination and for directing a resulting retinal image toward an image storage device which includes a video camera; and
an optical filter positioned between the retina and the image storage device for blocking the infrared illumination from entering the image storage device, the optical filter having a sharp cut-off response matched to the excitation and emission peak wavelengths of the infrared fluorescent dye so that the filter substantially passes emission peak wavelengths and substantially blocks excitation peak wavelengths.

48. The apparatus of claim 47 wherein the illumination source operates continuously to provide for real time video recording by the video camera.

49. An apparatus for imaging retina, comprising:
a narrow bandwidth, non-coherent, and decollimated infrared illumination-producing illumination source which is matched to an excitation peak of ICG dye;

an optical system for directing narrow bandwidth, non-coherent, and decollimated infrared illumination, which is produced by the source and matched to the excitation peak of the ICG dye, onto the retina of an eye under examination and for directing a resulting retinal image toward an image storage device; and an optical filter positioned between the retina and the image storage device for blocking the infrared illumination from entering the image storage device, the optical filter having a sharp cut-off response matched to excitation and emission peaks of ICG dye so that the filter substantially passes emission peak wavelengths and substantially blocks excitation peak wavelengths.

50. The apparatus of claim 49 wherein the optical filter blocks wavelengths below 820 nm.

* * * * *